US010634689B2

United States Patent
Lucas et al.

(10) Patent No.: US 10,634,689 B2
(45) Date of Patent: Apr. 28, 2020

(54) METHODS FOR CANNABINOID QUANTIFICATION

(71) Applicant: Compassionate Analytics Inc., Victoria (CA)

(72) Inventors: Philippe Lucas, Victoria (CA); Caleb Eades, Gabriola Island (CA)

(73) Assignee: Compassionate Analytics Inc., Victoria, British Columbia (CA)

( * ) Notice: Subject to any disclaimer, the term of this patent is extended or adjusted under 35 U.S.C. 154(b) by 0 days.

(21) Appl. No.: 15/863,506

(22) Filed: Jan. 5, 2018

(65) Prior Publication Data

US 2018/0128843 A1 May 10, 2018

Related U.S. Application Data

(63) Continuation of application No. 15/587,162, filed on May 4, 2017, now abandoned, which is a continuation of application No. 14/771,592, filed as application No. PCT/CA2014/000157 on Feb. 28, 2014, now abandoned.

(60) Provisional application No. 61/771,263, filed on Mar. 1, 2013, provisional application No. 61/827,128, filed on May 24, 2013.

(51) Int. Cl.
| | | |
|---|---|---|
| *G01N 33/94* | (2006.01) | |
| *G01N 33/52* | (2006.01) | |
| *G01N 21/78* | (2006.01) | |
| *G01N 33/53* | (2006.01) | |

(52) U.S. Cl.
CPC ........... *G01N 33/948* (2013.01); *G01N 21/78* (2013.01); *G01N 33/52* (2013.01); *G01N 33/523* (2013.01); *G01N 33/5302* (2013.01)

(58) Field of Classification Search
CPC .... G01N 33/52; G01N 33/5302; G01N 33/94; G01N 33/948; G01N 21/77; G01N 21/78; Y10T 436/14; Y10T 436/142222; Y10T 436/20; Y10T 436/203332; Y10T 436/25; Y10T 436/25375; Y10T 436/255
USPC ... 436/91, 93, 127, 131, 164, 169, 174, 177, 436/178; 422/400, 420, 430, 68.1, 82.09
See application file for complete search history.

(56) References Cited

U.S. PATENT DOCUMENTS 3,955,926 A * 5/1976 Fischer ................. G01N 31/22
436/92
4,771,005 A * 9/1988 Spiro ................. C09B 67/0079
422/400

(Continued)

FOREIGN PATENT DOCUMENTS

| GB | 1388221 | * | 3/1975 |
| WO | 89/09395 | * | 10/1989 |

OTHER PUBLICATIONS

Mechoulam et al. Abstract from Tetrahedron, vol. 24, issue 16, 1968, pp. 5615-5624.*

*Primary Examiner* — Maureen Wallenhorst
(74) *Attorney, Agent, or Firm* — Snell & Wilmer L.L.P.

(57) ABSTRACT

A method for quantification of the concentration of one or more cannabinoid compounds in a liquid sample is provided. The method involves contacting the liquid sample with at least one cannabinoid-sensitive visualization reagent, allowing the at least one cannabinoid-sensitive visualization reagent to develop for a defined amount of time; and comparing the resulting color change of the at least one cannabinoid-sensitive visualization reagent to a calibrated quantification reference chart.

17 Claims, 7 Drawing Sheets

(56) References Cited

U.S. PATENT DOCUMENTS

| | | | |
|---|---|---|---|
| 6,391,261 B1* | 5/2002 | Liang | G01N 33/84 |
| | | | 422/401 |
| 7,700,368 B2* | 4/2010 | Flockhart | C07D 311/80 |
| | | | 436/177 |
| 2004/0053419 A1* | 3/2004 | Keizer | G01N 33/54386 |
| | | | 436/169 |
| 2005/0079629 A1* | 4/2005 | Guo | G01N 33/521 |
| | | | 436/169 |
| 2006/0008920 A1* | 1/2006 | Wong | G01N 33/523 |
| | | | 436/514 |
| 2007/0077660 A1* | 4/2007 | Glas | G01N 30/90 |
| | | | 436/93 |
| 2011/0117664 A1* | 5/2011 | Amisar | G01N 31/22 |
| | | | 436/164 |
| 2015/0017732 A1* | 1/2015 | Wu | G01N 31/22 |
| | | | 436/92 |

* cited by examiner

METHODS FOR CANNABINOID QUANTIFICATION

CROSS REFERENCE TO RELATED APPLICATIONS

This application is a continuation application of U.S. Non-Provisional application Ser. No. 15/587,162, filed May 4, 2017, entitled "Methods for Cannabinoid Quantification", which is a continuation application of U.S. Non-Provisional application Ser. No. 14/771,592, filed Aug. 31, 2015, entitled "Methods for Cannabinoid Quantification", which is a U.S. National Stage Entry Application of International Application Serial Number PCT/CA2014/000157, filed Feb. 28, 2014, entitled "Methods for Cannabinoid Quantification", which claims priority to U.S. Provisional Patent Application Ser. No. 61/771,263, filed Mar. 1, 2013, entitled "Cannabinoid Quantification", U.S. Provisional Patent Application Ser. No. 61/827,128, filed May 24, 2013 entitled "Cannabinoid Quantification, In Solution" and, U.S. Provisional Patent Application Ser. No. 61/884,409, filed Sep. 30, 2013, entitled "Cannabinoid Quantification," all of which are hereby incorporated by reference for all purposes.

FIELD OF THE INVENTION

The present invention relates to compositions and methods for accurate quantification of cannabinoid compounds in a sample.

BACKGROUND OF THE INVENTION

The legal production, sale and use of *cannabis* for medical purposes is becoming more prevalent in many countries, including the United States and Canada. It is important for medical *cannabis* growers, dispensaries and end-users to know the concentration of certain cannabinoids, particularly delta-9-tetrahydrocannabinol (THC) in specific plant samples—such information can be important for strain development, for optimizing production/growing cycles, for complying with jurisdiction-specific legal requirements, and for other quality control purposes. Quantification of cannabinoids in a sample generally requires a laboratory test, for instance using gas chromatography, which can be expensive and generally requires time to send the sample to an appropriate lab and wait for the results. Home-based tests, such as Alpha-Cat, have been developed using thin-layer chromatography, however this test is still quite complex for the average untrained user, and the quantification resolution of the test is limited.

Reagents are known in the art that react chemically with CBD, under specific reaction conditions, to create a color change. Mechoulam (Tetrahedron 24(16): 5615-5624, 1968) teaches that CBD, when contacted with 5% ethanolic potassium hydroxide (KOH) is converted to quinone, which has a purple color.

U.S. Pat. No. 4,771,005, issued to Spiro, teaches methods for positive/negative cannabinoid detection in human sample using a diazonium salt, for instance Fast Blue BB.

WO/1989/009395 (published in the name of Fraser and Johnson) teaches a test paper for positive/negative cannabinoid detection using diazonium salt, for instance Fast Blue BB.

U.S. Pat. No. 8,124,420, issued in the name of Amisar, teaches a test paper and kit for detection and/or identification of a range of drugs of abuse, which may include cannabinoids, and the test paper may include a diazonium salt, for instance Fast Corinth V.

Fischedick et al. (2009 Phytochem Anal 20:421-6) teaches a method for quantifying cannabinoids in a sample using high performance thin layer chromatography (HPTLC).

SUMMARY OF THE INVENTION

In one aspect of the invention, a method for quantification of the concentration of one or more cannabinoid compounds in a liquid sample is provided. The method involves contacting the liquid sample with at least one cannabinoid-sensitive visualization reagent; allowing the at least one cannabinoid-sensitive visualization reagent to develop for a defined amount of time; and comparing the resulting color change of the at least one cannabinoid-sensitive visualization reagent to a calibrated quantification reference chart. The at least one cannabinoid-sensitive visualization reagent may be present in a liquid form. The at least one cannabinoid-sensitive visualization reagent may be present in a solid form. The liquid sample may be contacted separately with the at least one cannabinoid-sensitive visualization reagent. The at least one cannabinoid-sensitive visualization reagent may be impregnated in a test strip. The test strip may include a porous matrix uniformly impregnated with the at least one cannabinoid-sensitive visualization reagent. The at least one cannabinoid-sensitive visualization reagent reacts with cannabinoids, which can include THC, CBD, or CBN. Optionally, the cannabinoid may be solely THC, CBD or another cannabinoid. The at least one cannabinoid-sensitive visualization reagent may include one or more diazonium salts, a Duquenois reagent, a Ghamrawy reagent, or a modified Ghamrawy reagent. The one or more diazonium salts may include Fast Blue B, Fast Blue BB, Fast Red B, Fast Red GG, Fast Orange GR, Fast Corinth V, Fast Garnet GC, Fast Red AV, or Fast Bordeaux GP. Optionally, the at least one cannabinoid-sensitive visualization reagent may be a strong base, which may be potassium hydroxide or sodium hydroxide. Further, the at least one cannabinoid-sensitive visualization reagent may be impregnated in a test strip. Further still, the test strip may include a porous matrix uniformly impregnated with the at least one cannabinoid-sensitive visualization reagent.

In another aspect of the invention, a method for quantification of one or more cannabinoid compounds in a solid test sample is provided. The method involves contacting the solid test sample with an extraction solvent, wherein one or more cannabinoids are extracted from the solid sample into an extraction solvent resulting in a cannabinoid-containing liquid extraction solution; contacting the cannabinoid-containing liquid extraction solution with one or more cannabinoid-sensitive visualization reagents; and comparing the intensity of the resulting color change of the one or more cannabinoid-sensitive visualization reagents to a calibrated quantification reference chart.

In another aspect of the invention, an apparatus which includes a test strip impregnated with at least one cannabinoid-sensitive visualization reagent is disclosed. Optionally the at least one cannabinoid-sensitive visualization reagent may be one or more diazonium salts, a Duquenois reagent, a Ghamrawy reagent, a modified Ghamrawy reagent, and potassium hydroxide.

In another aspect of the invention, a kit for quantification of the concentration of one or more cannabinoid compounds in a sample is disclosed. The kit includes at least one cannabinoid sensitive visualization reagent, and a calibrated quantification reference chart. Optionally, the at least one cannabinoid-sensitive visualization reagent is present in a liquid form or a solid form. Further and optionally, the at least one cannabinoid-sensitive visualization reagent is pre-measured as a dry reagent in one or more reaction containers. Further still, the at least one cannabinoid-sensitive visualization reagent is impregnated into a test strip.

Aspects of the present invention are based, in part, on the finding that certain cannabinoid-sensitive visualization reagents may be used to quantify the cannabinoid concentration in a sample. Herein, it has been demonstrated that the use of one or more cannabinoid-sensitive visualization reagents which cause an absorbance shift (color change) in a solution upon contact with cannabinoids including THC and/or CBD, may be utilized to quantify the concentration of such cannabinoids in a given sample. Quantification is achieved by contacting the one or more cannabinoid-sensitive visualization reagents with a liquid cannabinoid-containing sample, or alternatively with a liquid extraction from a solid cannabinoid-containing sample, and comparing the resulting absorbance shift to that caused by samples with known cannabinoid concentrations. Herein, examples have been provided of such assays to determine the concentration of THC, CBD, and/or other cannabinoids in a solid plant test sample, or a liquid test sample. Examples have been provided of a calibrated quantification reference chart, useful in said assay, calibrated to determine the cannabinoid concentration in a solid plant test sample, and suitable for solid plant test samples having cannabinoid concentration ideally between 0-25%, but potentially higher. In some embodiments, the calibrated quantification reference chart has been optimized for this cannabinoid concentration range by extracting cannabinoids from series of solid samples having known cannabinoid concentrations ranging from 0% to 25%, using a consistent and uniform extraction solvent composition, volume, and extraction time for all of the samples, and contacting the resulting cannabinoid-containing extraction liquid with a defined amount of one or more cannabinoid-sensitive visualization reagents. The resulting absorbance shift, or color change, caused by each of the samples of known cannabinoid concentration provides a calibrated quantification reference chart for use in the experimental assay for the test sample—by extracting the cannabinoids from the unknown test sample using the exact same extraction solvent composition, volume, and extraction time; contacting the resulting cannabinoid-containing extraction liquid with the same amount/concentration of the one or more cannabinoid-sensitive visualization reagents; and comparing the resulting absorbance shift(s), or color change(s), with the calibrated quantification reference chart, one may thus determine the cannabinoid concentration in the unknown solid test sample. In the examples provided herein, the extraction solvent composition, volume, and extraction time have been optimized to ensure that the absorbance shift caused by contacting the resulting cannabinoid-containing extraction solution with the one or more cannabinoid-sensitive visualization reagents is in the optimized range of the visualization reagent, such that the absorbance, or color change intensity, is proportional to the cannabinoid concentration in the test sample. In certain aspects of the invention, the cannabinoid that may be quantified is one or more of THC, CBD and/or CBN, and the cannabinoid-sensitive visualization reagent one or more of: i) diazonium salt, for instance Fast Blue B, Fast Blue BB, Fast Blue RR, Fast Corinth V, Fast Garnet, Fast Bordeaux, and the like; ii) a Duquenois reagent; and iii) a Ghamrawy reagent or modified Ghamrawy reagent. In certain aspects of the invention, the cannabinoid that may be quantified is CBD, and the cannabinoid-sensitive visualization reagent is a strong base for instance potassium hydroxide or sodium hydroxide, wherein the medium in which the strong base contacts the CBD is methanol, ethanol, propanol, or another lower alcohol solvent.

Examples have been provided of a variety of visualization reaction compositions and methods suitable for the present invention. In certain aspects of the invention, the visualization reaction may occur in a liquid solution, wherein the one or cannabinoids of the liquid test sample, or extracted from the solid test sample, are contacted with the one or more cannabinoid-sensitive visualization reagents in solution, for instance using a solvent composition that is permissive for the visualization reaction. In certain aspects, the cannabinoids of the test sample are separately contacted with each of the one or more cannabinoid-sensitive visualization reagents in separate reaction vessel. In other aspects of the invention, the visualization reaction may be accomplished using a test paper, wherein the test paper is impregnated with a cannabinoid-sensitive visualization reagent. In certain aspects, the test paper may be a test strip comprising one or more test pads, wherein each test pad is impregnated with a different cannabinoid-sensitive visualization reagent. In this regard, one of unique features of the present invention is based in part on the finding that certain cannabinoid-sensitive visualization reagents have different, and potentially overlapping, quantification ranges and/or sensitivities. Thus, in certain aspects of the present invention, the use of more than one cannabinoid-sensitive visualization reagent may allow for an extended range and accuracy of quantification. Another feature is that certain cannabinoid sensitive visualization reagents may be impregnated on a test strip and included in a kit in such a way that the activity of the visualization reagent is retained when the strip is eventually used by the end-user.

BRIEF DESCRIPTION OF THE FIGURES

Two sets of identical figures are being submitted herewith: a first set rendered in black and white, and a second set is rendered in colour.

DETAILED DESCRIPTION

Figure 1:
FIG. 1 depicts a calibrated quantification reference chart for THC samples having an ideal range of 5-20%. The quantification reference chart was generated using Fast Blue BB. The chart shows a light yellow colour at the left side, changing to a darker yellow/orange on the right side.

Any terms not directly defined herein shall be understood to have the meanings commonly associated with them as understood within the art of the invention. As employed throughout the specification, the following terms, unless otherwise indicated, shall be understood to have the following meanings.

The term 'sample' means a complex substance that may be tested or analyzed for the presence of certain compounds. A 'sample' may be a liquid sample or a solid sample. A liquid sample may comprise a bodily fluid such as urine or blood. A liquid sample may comprise a solvent extract of a solid sample, wherein various compounds from the solid sample are extracted into the liquid solvent using methods known in the art. A solid sample may include plant material, for instance *cannabis* plant material.

The term '*cannabis*' means a genus of flowering plants that includes three putative species, *Cannabis sativa*, *Cannabis indica*, and *Cannabis ruderalis*. The term '*cannabis*' may also refer to plant material derived or extracted from the *cannabis* plant, for instance the leaves, stem, seeds, flowering bodies, or other portions of the plant.

The term 'cannabinoid' or 'cannabinoids' means a class of chemical compounds which include the phytocannabinoids (oxygen-containing C21 aromatic hydrocarbon compounds found in the *cannabis* plant), and chemical compounds which mimic the actions of phytocannabinoids or have a similar structure (e.g., endocannabinoids, found in the nervous and immune systems of animals and that activate cannabinoid receptors). Phytocannabinoids are known to occur in significant quantities in the *cannabis* plant, and may include, but are not limited to tetrahydrocannabinol (THC), cannabidiol (CBD), cannabinol (CBN), and cannabigerol (CBG).

The term 'THC' means tetrahydrocannabinol and may include different isoforms and variants, such as delta-9-Tetrahydrocannabinol ($\Delta$9-THC) and delta-8-tetrahydrocannabinol ($\Delta$8-THC). The inventors herein disclose methods and an apparatus for quantification of THC and/or other cannabinoids from a sample, for instance from a solid *cannabis* sample.

The term 'CBD' means cannabidiol, a cannabinoid often found in *cannabis*, and having a CAS registry number 13956-29-1. Cannabidiol is known to have many beneficial medicinal qualities.

The term 'extraction' means to transfer compounds from a sample into another medium, for instance into a liquid solvent. The solvent may be chosen such that certain desired compounds are soluble in the solvent, and thus when the sample is contacted with the solvent, the desired compounds are transferred to the solvent. Extraction of solid samples may be aided or enhanced by grinding, macerating or otherwise pulverizing the sample material. Extraction is aided by shaking, vortexing or otherwise mixing the solvent with the sample. Uniform extraction yields may be achieved by using defined extraction methods, including duration of extraction, solvent composition, and the like. In certain embodiments, a solid sample may be heated prior to extraction—this may serve to chemically convert certain compounds that are not soluble in the extraction solvent into compounds that are soluble in the extraction solvent. Furthermore, the converted compounds may be more reactive with visualization reagents. In certain embodiments of the invention, solid *cannabis* samples are heated prior to extraction in order to decarboxylate the acid form of THC, CBD, etc. into non-acid forms which are more readily extracted and more readily react with the visualization reagents of the present invention. Ideally, the heat conversion is carried out a temperature that is below the volatilization temperature of the cannabinoids, but above the decarboxylation temperature. In this way, any THC-A and CBD-A in the solid sample, may be converted to THC and CBD prior to extraction, and the subsequent visualization reactions of the invention will give a more accurate quantification of total THC and/or total CBD in the sample.

A 'visualization reagent' means a reagent or compound that changes color upon contact with a particular analyte or class of analytes, or alternatively causes the analyte to change color upon contact with the visualization reagent, or alternatively causes a color change in a reaction medium containing a particular analyte or class of analytes. The change in color will result in a change in the spectral absorbance of the reaction medium, detection of which may be visible to the naked eye, or may be more accurately quantified using a device such as a colorimeter, spectrometer, spectrophotometer, or the like. Visualization reagents may alternatively be referred to as colorimetric reagents. There are numerous types of visualization reagents described in the art. Certain visualization reagents may be suitable for quantification of analytes, while others may not. Suitable visualization reagents may cause a color change that is proportional to the concentration of the analyte, over a specific analyte concentration range—sometimes referred to as the 'linear range' or 'optimal range' of the visualization reagent. The optimal range of the visualization reagent for the specific analyte must be wide enough to provide quantification information across a sufficient range to be a useful visualization reagent. A visualization reaction may require contacting the visualization reagent with the analyte in reaction conditions suitable to cause the appropriate chemical reaction. For instance, a suitable solvent may be used to facilitate the visualization reaction. The suitable solvent of the present invention may be an alcohol such as methanol, ethanol, propanol and the like.

A 'diazonium salt', or 'diazonium compound', is a compound belonging to a group of organic compounds sharing a common functional group R—N2+ X– where R can be any organic residue such alkyl or aryl and X is an inorganic or organic anion such as a halogen. Diazonium salts, especially those where R is an aryl group, are important intermediates in the organic synthesis of azo dyes. Diazonium salts are often used as visualization reagents by conversion of the diazonium salt into an azo dye, such conversion causing a change in absorbance. Examples of diazonium salts may include, but are not limited to, Fast Blue B (3,3'-dimethoxybenzidine (o-dianisidine)), Fast Blue BB (4-Benzoylamino-2,5-diethoxyaniline), Fast Red B (2-Methoxy-4-nitroaniline), Fast Red GG (4-Nitroaniline), Fast Orange GR (2-Nitroaniline), Fast Corinth V (2-methoxy-5-methyl-4-(4-methyl-2-nitrophenyl)-azobenzene-diazonium), Fast Garnet GC (4-(m-Tolylazo)-3-methylaniline), Fast Red AV, and Fast Bordeaux GP.

A 'Duquenois reagent' is a reagent used in a Duquenois-Levine test for detecting *cannabis* (see: P. Duquenois and H. N. Moustapha, J. Egypt. Med. Ass., 1938, 21, 224.) A Duquenois reagent may comprise a mixture of vanillin and acetaldehyde, along with hydrochloric acid. In certain embodiments, the hydrochloric acid may be substituted for another acid. In certain embodiments, the strong acid may be present as a dry form, for instance p-toluenesulfonic acid, and may be impregnated in a test paper/strip.

A 'Ghamrawy reagent' refers to a combination of compounds that may be used for detection of THC and CBD. A Ghamrawy reagent is further described in: Kovar, Karl-Artur and Martina Laudszun. (Chemistry and Reaction Mechanisms of Rapid Tests for Drugs of Abuse and Precursors Chemicals, United Nations Scientific and Technical Notes v. 89-51669, Germany. February 1989. The Ghamrawy reagent consists of p-dimethylaminobenzaldehyde (p-DMAB) along with concentrated sulfuric or hydrochloric acid. In certain embodiments, the Ghamrawy reagent may be modified—the inventors have identified other strong acids that may be useful for catalyzing the color reaction with p-DMAB. For instance, p-toluenesulfonic acid that may be used instead of hydrochloric acid or sulfuric acid. This acid is advantageous for use in test strips, by virtue of the fact that p-toluenesulfonic acid may be present as a solid, whereas hydrochloric and sulfuric acid generally are not. Furthermore p-toluenesulfonic acid is non-corrosive and thus will not degrade the test strip. This surprising finding has enabled the use of test papers/strips impregnated with the modified Ghamrawy reagent for quantification of THC and/or CBD. Thus, a 'modified Ghamrawy reagent' comprises p-DMAB and a strong acid, for instance p-toluenesulfonic acid. Other strong acids that may be present as a solid may also be used in a modified Ghamrawy reagent.

The term 'KOH' means 'potassium hydroxide'. Potassium hydroxide may have the CAS registry number 1310-58-3. The term 'NaOH' means 'sodium hydroxide. Sodium hydroxide may have the CAS registry number 1310-73-2.

The term 'cannabinoid-sensitive visualization reagent' refers to a reagent such as a visualization reagent that undergoes a change in properties, such as spectral absorbance, upon contact with a cannabinoid. In the context of the present invention, the change in chemical properties may occur due to a change in either reactant in the visualization reaction, or even a change in the reaction medium itself. Alternatively, the change in chemical properties may occur due to the formation of a new compound, such as a reaction by-product. A cannabinoid-sensitive visualization reagent may be a diazonium salt. Certain diazonium salts are known to cause a change of color in the presence of cannabinoids such as THC, CBD and/or CBN—such diazonium salts include, but are not limited to, Fast Blue B, Fast Blue BB, Fast Corinth V, and Fast Garnet GC. A cannabinoid-sensitive visualization reagent may be a Duquenois reagent. A cannabinoid-sensitive visualization reagent may be a Ghamrawy reagent or a modified Ghamrawy reagent. A cannabinoid-sensitive visualization reagent may be potassium hydroxide or sodium hydroxide.

The term 'permissive' or 'permissive solvent' refers to solvents that have a composition that allow the desired chemical reaction to occur. For instance, certain chemical reactions may proceed much more readily in an alcohol than in water. In such case, the alcohol would be a permissive solvent and would be the desired solvent for the reaction. In various embodiments, the use of permissive solvents is important for the utility of the invention.

The term 'calibrated quantification reference chart' means a chart, graph, or other visual representation showing the specific absorbance shift or color change of one or more specific visualization reagents caused by a specific analyte across a range of specific concentration, under specific conditions, such that comparison of an analyte at an unknown concentration, using the same one or more specific visualization reagents under the same specific conditions, to the calibrated quantification reference chart will allow one to determine the concentration of that analyte in the unknown test sample. The specific absorbance shift or color change may be determined for instance using a test paper, test strip, a colorimeter, a spectrometer, or by visual inspection. The present invention utilizes a calibrated quantification reference chart to determine the concentration of cannabinoids in a sample. In certain embodiments of the invention, a calibrated quantification reference chart may be used or created for determining the cannabinoid concentration in an unknown solid sample by extracting cannabinoids from series of solid samples having known cannabinoid concentrations, using a uniform extraction solvent composition, volume, and extraction time for all of the samples, and contacting the resulting cannabinoid-containing extraction liquid with a defined amount of one or more cannabinoid-sensitive visualization reagents. The resulting absorbance shift(s), or color change(s), caused by each of the samples of known cannabinoid concentration provides a calibrated quantification reference chart for use in the experimental assay for the unknown test sample. By then extracting the cannabinoids from the unknown test sample using the exact same extraction solvent composition, volume, and extraction time; contacting the resulting cannabinoid-containing extraction liquid with the same amount/concentration of one or more cannabinoid-sensitive visualization reagents; and comparing the resulting absorbance shift(s), or color change(s), with the calibrated quantification reference chart, one may thus determine the cannabinoid concentration in the unknown solid sample.

The term 'porous matrix' refers to a solid material, ie. a matrix, that is permeated with pores or small holes to allow absorbance of a fluid into the matrix. A porous matrix may be a type of paper or filter, such as blotting paper. Examples of a porous matrix include Whatman paper, CF1, CF2, CF3, cellulose paper, and the like.

The term 'test paper' refers to a porous matrix which is impregnated with a diagnostic reagent, for instance a cannabinoid-sensitive visualization reagent such as a diazonium salt, Duquenois reagent, Ghamrawy reagent, or modified Ghamrawy reagent. Impregnation of the porous matrix with the reagent may be accomplished in several different ways. The reagent to be impregnated into the porous matrix to form the test paper may first be dissolved in a suitable solvent, and the porous matrix then contacted with or submersed in the resulting solution containing the dissolved reagent. For instance, the solvent may be an alcohol such as methanol, ethanol or propanol. Preferably, the solvent may be a ketone such as acetone or methyl ethyl ketone—these solvent may prevent degradation of the dye and reduce background coloration on the test strips. Evaporation of the solvent will result in a dry test strip impregnated with the reagent. Suitable solvents should thus be chosen such that the reagent is miscible in the solvent, and such that the solvent is volatile enough to effectively evaporate away from the porous matrix. Examples of suitable solvents include, but are not limited to, water, methanol, ethanol, isopropanol, petroleum ether, methyl ethyl ketone, acetone, dimethylchloride, hexane. In certain embodiments, the visualization reagent may be heated after impregnation of the test paper, or during the drying of the test paper. Such heating may activate the visualization reagent. In certain embodiments the test paper may be subsequently sealed into an air tight package, for instance by vacuum sealing. This may preserve the activation or activity of the visualization reagent. A test paper may be contacted with a test compound, for instance a cannabinoid, in a suitable solvent, and the reaction of the test compound with the diagnostic reagent may cause the test paper to change color. In various embodiments of the invention, the color change of the test paper may be proportional to the concentration of one or more cannabinoids in the solution, and may thus be used to quantify the cannabinoid concentration.

The term 'test strip' refers to a strip of material to which is attached one or more test papers. A test strip may be elongated to allow for ease of contacting with the test solution, for instance by dipping into a test tube or the like. The test strip may include i) a backing material, which may be absorbent or non-absorbent, and is preferentially but not necessarily inert; ii) one or more test papers comprising one or more cannabinoid-sensitive visualization reagents; and iii) an adhesive to attach the one or more test papers to the backing material.

Quantification of cannabinoid concentration in liquid or solid samples using one or more cannabinoid-sensitive visualization reagents.

Herein, the inventors describe methods for determination of the cannabinoid concentration in liquid or solid samples using one or more cannabinoid-sensitive visualization reagents. The inventors have surprisingly determined that certain cannabinoid-sensitive visualization reagents can be utilized in conjunction with a calibrated reference chart to determine the actual concentration of cannabinoids in a sample, rather than merely detecting the presence or absence of cannabinoids, and are thus suitable for cannabinoid quantification. In certain embodiments of the invention, such one or more cannabinoid-sensitive visualization reagents are first contacted with a cannabinoid-containing liquid sample, or with a liquid extraction of a cannabinoid-containing solid sample, under conditions which cause a color change or absorbance shift of the one or more visualization reagents, wherein such color change or absorbance shift is proportional to the cannabinoid concentration. The color change or absorbance shift of the visualization reagent is then compared to a calibrated quantification reference chart, wherein the calibrated quantification reference chart is created by testing a series of liquid or solid sample of known cannabinoid concentration under the exact same test conditions as the sample of unknown concentration—ideally the calibrated quantification reference chart would show the color change or absorbance shift at a number of known cannabinoid concentrations. In such a way, one may compare the color change or absorbance shift of the sample of unknown cannabinoid concentration to the calibrated quantification reference chart to determine the cannabinoid concentration in the unknown sample. Determination of the color change or absorbance shift may be accomplished by numerous means, for instance using a colorimeter or spectrophotometer, or by visual inspection. In certain embodiments, the one or more cannabinoid-sensitive visualization reagents is a diazonium salt, such as Fast Blue B, Fast Blue BB, Fast Corinth V, Fast Garnet GC, and the like, which are useful for quantification of THC, CBD and/or CBN. In other embodiments, the cannabinoid-sensitive visualization reagent is a strong base, for instance potassium hydroxide or sodium hydroxide, useful for quantification of CBD. In other embodiments, the one or more cannabinoid-sensitive visualization reagents is a Duquenois reagent, a Ghamrawy reagent, or a modified Ghamrawy reagent.

In one embodiment of the invention, there is provided a method for quantification of the concentration of one or more cannabinoid compounds from a liquid test sample, the method involves: 1) contacting the cannabinoid-containing liquid sample with a defined amount of one or more cannabinoid-sensitive visualization reagents; 2) allowing the resulting visualization reaction(s) to develop for a defined amount of time; and 3) comparing the intensity of the resulting color change, or absorbance shift, of the one or more cannabinoid-sensitive visualization reagents to a calibrated quantification reference chart, wherein such comparison allows determination of the cannabinoid concentration in the test sample. The calibrated quantification reference chart may be produced, for instance, by contacting a series of calibrated liquid samples having pre-determined cannabinoid concentrations with the same amount/composition of one or more cannabinoid-sensitive visualization reagents under the exact same conditions as to be used for the unknown test sample, including using the same one or more cannabinoid-visualization reagents and the same color development time as to be used for the test sample. In certain embodiments wherein two or more cannabinoid-sensitive visualization reagents are used, each visualization reagent may be separately contacted with the cannabinoid(s) of the test sample. In certain embodiments, the method may be useful for the quantification of cannabinoids THC, CBD and/or CBN in a liquid sample. The one or more cannabinoid-sensitive visualization reagents may be a diazonium salt. The one or more cannabinoid-sensitive visualization reagents may be chosen from the following: Fast Blue B, Fast Blue BB, Fast Blue RR, Fast Corinth V, Fast Garnet, Fast Bordeaux. The diazonium salt(s) and the cannabinoids may be contacted in permissive solvent. The one or more cannabinoid-sensitive visualization reagents may be a Duquenois reagent, a Ghamrawy reagent, and/or a modified Ghamrawy reagent. In other embodiments, the method may be useful for the quantification of CBD in a liquid sample. The cannabinoid-sensitive visualization reagent may be a strong base, for instance potassium hydroxide, sodium hydroxide. The strong base, for instance potassium hydroxide, and/or cannabinoid(s) may be contacted in a permissive solvent such as a lower alcohol, for instance methanol, ethanol, propanol, and the like.

In another embodiment of the invention, there is provided a method for quantification of one or more cannabinoid compounds in a solid test sample, the method involves: 1) contacting a defined amount of solid test sample with a defined volume of an extraction solvent for a defined amount of time, wherein one or more cannabinoids are extracted from the solid sample into an extraction solvent resulting in a cannabinoid-containing liquid extraction solution; 2) contacting the resulting cannabinoid-containing liquid extraction solution with defined amount of one or more cannabinoid-sensitive visualization reagent; 3) allowing the resulting visualization reaction(s) to develop for a defined amount of time; and 4) comparing the intensity of the resulting color change, or absorbance shift, of the one or more cannabinoid-sensitive visualization reagents to a calibrated quantification reference chart, wherein such comparison allows determination of the cannabinoid concentration in the solid test sample. The calibrated quantification reference chart may be produced by performing the same assay method on a series of solid samples having known cannabinoid concentrations and recording the resulting absorbance changes. For instance, the calibrated quantification reference chart may be produced by contacting a series of solid samples having pre-determined cannabinoid concentrations with the same defined amount of the same defined extraction solvent composition, and then contacting a defined amount of resulting cannabinoid-containing extraction solution with one or more cannabinoid-sensitive visualization reagents under the exact same conditions as to be used for each test sample, including using the same one or more cannabinoid-visualization reagent compositions and concentrations, and the same color development time as to be used for the test sample. In certain embodiments wherein two or more cannabinoid-sensitive visualization reagents are used, each visualization reagent is separately contacted with the cannabinoid(s) of the test sample. In certain embodiments, the method may be useful for quantification of the concentration cannabinoids THC, CBD and/or CBN in a solid test sample. The one or more cannabinoid-sensitive visualization reagent may be a diazonium salt. The cannabinoid-sensitive visualization reagent may be chosen from the following: Fast Blue B, Fast Blue BB, Fast Blue RR, Fast Corinth V, Fast Garnet, Fast Bordeaux. The diazonium salt(s) and the cannabinoids may be contacted in permissive solvent. The cannabinoid-sensitive visualization reagent may be a Duquenois reagent, a Ghamrawy reagent, or a modified Ghamrawy reagent. In certain embodiments, the method may be useful for the quantification of CBD in a solid test sample. The cannabinoid-sensitive visualization reagent may be a strong base, for instance potassium hydroxide, sodium hydroxide. The strong base, for instance potassium hydroxide, and/or cannabinoid(s) may be contacted in a permissive solvent such as a lower alcohol, for instance methanol, ethanol, propanol, isopropanol, etc.

Extended Range of Quantification

Herein, cannabinoid quantification assays are described which have an extended range of quantification. The cannabinoid quantification assays described in various embodiments of the invention all have a lower and upper limit of quantification, below and above which quantification is relatively ineffective. Below the lower limit of quantification, the cannabinoid concentration is too low to cause a significant absorbance shift, or color change, from the cannabinoid-sensitive visualization reagent. Above the upper limit of quantification, the absorbance shift, or color change, may become saturated such that no further color change may be detected, even with an increased concentration of the test analyte. Optimal quantification results are thus achieved between the lower and upper limits of quantification, and the greater the distance between these two values, the more useful the assay may be—suitable visualization reagents must be tested and selected in order to obtain a useful quantification assay. Since cannabinoids may exist at wide range different concentrations in a particular sample, it would be desirable to develop assays with extended ranges. In order to accomplish this, the present inventors take advantage of the fact that different visualization reagents, such as cannabinoid-sensitive visualization reagents, often have different sensitivity to, and/or optimal ranges for, the test compound in question, for instance cannabinoids. These different visualization reagents may have different lower and upper limits of quantification, and thus different effective quantification ranges. In fact, certain visualization reagents may have overlapping quantification ranges, which may be useful for developing an extended range assay method using multiple visualization reagents.

In certain embodiments of the invention, there is provided an extended range cannabinoid quantification assay method involving the use of two or more cannabinoid-sensitive visualization reagents, useful for quantification of cannabinoids in a liquid or solid test sample. The extended range cannabinoid quantification assay method may have certain advantages over assay methods using a single visualization reagent. The assay method may be carried out using the same steps as described in other aspects of the invention that use a single visualization reagent (described herein), except that two or more visualization reactions are carried out in parallel, for instance in separate tubes or on separate test papers, and the absorbance shift, or color change, of each of the visualization reactions is compared to a calibrated reference chart, wherein the calibrated reference chart shows the calibrated quantification values for each of the two or more cannabinoid-sensitive visualization reagents used in the assay. In certain embodiments of the invention, the assay method may be useful for quantification of cannabinoid concentrations across an extended range. In certain embodiments of the invention, the two or more cannabinoid-sensitive visualization reagents have differing cannabinoid sensitivity and or optimal quantification ranges. In certain embodiments of the invention, the optimal quantification ranges of each of the one or more visualization reagents are overlapping. The overlapping ranges allows for the quantification of cannabinoids in a sample across a wider range, which may improve the utility of the assay. For instance, and by way of non-limiting example, user may have a number of solid samples with expected THC %'s between 0 and 25%; the use of first single visualization reagent may allow optimal quantification of THC between 0-10% in the solid sample. The use of a second visualization reagent with an optimal quantification range of 10-25% would extend the overall optimal range of the assay to 0-25%. The use of additional cannabinoid-sensitive visualization reagents having even different quantification ranges may be used to further extend the quantification range of the assay method. It should be noted that the use of more than one visualization reagent can also improve the accuracy of quantification of cannabinoids in the overlapping region of the optimal quantification ranges of the visualization reagents, due to multiple readouts from the two or more visualization reagents. In certain embodiments of the invention, the two or more cannabinoid-sensitive visualization reagents may be diazonium salts and/or Duquenois-Levine reagent and/or Ghamrawy reagent and/or modified Ghamrawy reagent. In certain embodiments of the invention, the diazonium salts may be selected from: Fast Blue B, Fast Blue BB, Fast Blue RR, Fast Corinth V, Fast Garnet, Fast Bordeaux, or other cannabinoid-sensitive diazonium salts.

Visualization

In certain embodiments of the invention, methods are described for contacting cannabinoids from a test sample with one or more cannabinoid-sensitive visualization reagents, which results in an absorbance shift, or color change, suitable for quantification of the cannabinoids in the test sample. As exemplified in various working examples provided herein, the invention provides different compositions and methods useful for carrying out the visualization reaction. In certain embodiments, the visualization reaction may be carried out in a liquid solution, for instance in a reaction vessel such as a test tube, microtube, sample container, etc. A liquid solution of the cannabinoid-sensitive visualization reagent may be added to a liquid cannabinoid-containing solution, according to the methods of the present invention, and the color reaction may thus occur in solution. In certain embodiments of the invention, the cannabinoid-sensitive visualization reagent solution may be prepared fresh at the time of use.

An aspect of the present invention is to provide simple assays for cannabinoid quantification, and thus there are herein provided additional methods for reducing the number of required steps to complete the disclosed assays. These simplified assays are thus easier to use, have reduced handling which can increase accuracy, and are more cost effective. In certain cases, the simplification of the assays makes them more suitable for developing a test kit, as the modified steps may increase the shelf life of the reagents in the test kit. For instance, it is known that diazonium salt dyes such as Fast Blue B, Fast Blue BB, Fast Corinth V, etc. are inherently unstable in solution, particularly in aqueous solutions, and that this property has hindered the development of usable cannabinoid tests with this reagent, even for screening purposes. Thus, in certain embodiments of the invention, the diazonium salt visualization reagent may be provided in its dry powder form, and in certain aspects may be pre-measured in a defined amount in the reaction tube, or in a separate pouch to be added to the reaction tube. Other visualization reagents may similarly be provided in dry form. The user may then carry out the first steps of the quantification assay method in a first tube, thus extracting the cannabinoids from a solid sample in a defined amount of extraction solvent composition and volume, and then transfer a defined amount of the resulting cannabinoid-containing extraction liquid into a second tube containing a dry, pre-measured visualization reagent, and then mixing to dissolve the visualization reagent in the cannabinoid-containing extraction liquid, and comparing the resulting absorbance shift to a calibrated quantification reference chart. In the case of more than one visualization reagent, each may be provided in separate tubes. In certain embodiments of the invention, the diazonium salt may be stabilized as a salt of BF3, picric acid, sodium perchlorate, or other salts known in the art to stabilize such diazonium compounds, for instance as described in U.S. Pat. Nos. 4,771,005 and 8,124,420. In certain embodiments of the invention, the dry reagent may also include a solid diluent, preferable an inert solid diluent. The solid diluent may be useful for accurate measurement purposes, and may also serve as a dessicant and/or light protectant to aid in the stability of the dry reagent. In certain embodiments, the solid diluent may be soluble in the extraction solution to be used in the visualization reaction.

In another aspect of the invention, there is provided a simplified assay for quantification of CBD in a sample. Potassium hydroxide and sodium hydroxide are cannabinoid-sensitive visualization reagents that are specific for CBD. In general, to obtain an absorbance shift, the potassium hydroxide must be contacted with CBD in an ethanolic medium. The inventors have disclosed herein that an absorbance shift may also occur with potassium hydroxide in a methanolic medium, or other lower alcoholic media. Thus, in order to reduce the number of steps for the CBD quantification assays of the present invention, it would be desirable to extract the CBD from the sample using an extraction solvent such as methanol, ethanol, propanol, or other lower alcohols. In this way, the subsequent visualization reaction may be easily accomplished, by adding, for instance, solid potassium hydroxide in a pre-measured amount, or by adding a small amount of a concentrated potassium hydroxide solution, without a requirement to change the reaction medium, since the extracted CBD will be in a suitable solvent that is permissive for the visualization reaction with potassium hydroxide. This simplified assay may be particularly suitable for development of a test kit, since the visualization reagent, for instance potassium hydroxide or sodium hydroxide, may be provided in a non-alcoholic stock solution, such as an aqueous solution, that is more suitable for shipping and storage. Similarly, the visualization reagent, potassium hydroxide or sodium hydroxide may be provided in a concentrated form, in either alcoholic or non-alcoholic solution, thus allowing the addition of a very small amount, such as a drop or a few drops, without requiring the CBD containing extraction solution to be exchanged to a lower alcohol to allow the visualization reaction.

Test Papers and Strips

Certain embodiments of the invention are based, in part, on the surprising finding that test papers impregnated with certain cannabinoid-sensitive visualization reagents may be used to quantify the cannabinoid concentration in a sample. The inventor has provided examples of such test papers suitable for quantifying cannabinoids such as THC, CBD and/or CBN in a sample. Certain test papers are particularly useful for quantifying CBD in a test sample. Certain test papers are particularly useful for quantifying THC in a test sample. In these embodiments, the previously described methods for quantifying cannabinoids using cannabinoid-sensitive visualization reagents is accomplished by carrying out the visualization reaction on the test paper or test strip, rather than in solution in a reaction vessel.

CBD Test Papers and Strips

In certain embodiments, the cannabinoid-sensitive visualization reagent, for instance KOH or NaOH, is specific for CBD, and is present on the test paper in a sufficient amount to cause a colorimetric reaction on the test paper when the test strip is contacted with CBD in a permissive solvent. The permissive solvent may be an alcohol such as ethanol, methanol, or isopropanol. The inventors disclose that test strips impregnated with a CBD-specific cannabinoid-sensitive visualization reagent such as KOH, which undergoes an absorbance shift (changes color) upon contact with CBD in an appropriate solvent, may be utilized to quantify the concentration of such CBD in a given sample. Quantification is achieved by contacting the said test strip with a liquid CBD-containing sample (in a permissive solvent), or alternatively with a liquid extraction from a solid CBD-containing sample (in a permissive solvent), and comparing the resulting absorbance shift to that caused by samples with known CBD concentrations. The inventors have provided an example of such an assay to determine the concentration of CBD in a solid plant sample. The inventors have provided an example of a quantification reference chart, useful in said assay, calibrated to determine the CBD concentration in a solid plant sample, and suitable for solid plant samples having CBD concentration between 0-15%, and possibly higher. The calibrated reference chart has been optimized for this CBD concentration range by extracting cannabinoids from a series of solid samples having known CBD concentrations ranging from 0% to 15%, using a uniform extraction solvent composition, volume, and extraction time for all of the samples, and contacting the resulting CBD-containing extraction liquid with test strips impregnated with KOH. The resulting absorbance shift, or color change, caused by each of the samples of known CBD concentration provides a reference chart for use in the experimental assay for the unknown sample—by extracting the CBD from the unknown sample using the exact same extraction solvent composition, volume, and extraction time; contacting the resulting CBD-containing extraction liquid with the test papers impregnated with KOH; and comparing the resulting absorbance shift, or color change, with the calibrated quantification reference chart, one may thus determine the CBD concentration in the unknown solid sample. In an Example provided herein, the extraction solvent composition, volume, and extraction time have been optimized to ensure that the absorbance shift caused by contacting the resulting CBD-containing extraction solution with test papers impregnated with KOH is in the linear range of the visualization reagent, such that the absorbance, or color change intensity, is proportional to the CBD concentration. An important feature of the quantification method using the KOH-impregnated test papers is that the solvent used to extract or otherwise dissolve the CBD is of an appropriate composition to allow the visualization reaction to occur on the test paper. In an Example detailed herein, for instance, the KOH is dried onto the paper, and the CBD-containing test samples are dissolved in methanol or propanol, thus when the liquid test sample is contacted with the test strip, the methanol or propanol solvent creates an appropriate environment for the visualization reaction to occur between the KOH and CBD. In these various embodiments, the test papers may be affixed to a solid support, for instance to form a test strip, colorimetric strip, dipstick, and the like. As used herein, the terms 'test paper' and 'test strip' may be used interchangeably.

In one aspect of the invention, there is provided an apparatus including a test strip wherein the test strip comprises a porous matrix uniformly impregnated with a CBD-specific cannabinoid sensitive visualization reagent. The CBD-specific cannabinoid-sensitive visualization reagent may be a strong base. The CBD-specific cannabinoid-sensitive visualization reagent may be KOH or NaOH. In certain embodiments, the CBD-specific cannabinoid-sensitive visualization reagent is present on the test strip in sufficient amount to cause a colorimetric chemical reaction when contacted with CBD and a permissive solvent. The permissive solvent may be an alcohol. The permissive solvent may be ethanol, methanol, or propanol. In some embodiments, the CBD-specific cannabinoid-sensitive visualization reagent is present in the test paper in sufficient amount to allow quantification of CBD in a CBD containing sample.

In another aspect of the invention, there is provided a method for quantification of the concentration of CBD in a liquid sample, the method involves: 1) contacting the liquid sample with a test strip comprising a porous matrix uniformly impregnated with a CBD-specific cannabinoid-sensitive visualization reagent, wherein the liquid sample comprises a solvent of an appropriate composition to allow a colorimetric reaction between the CBD and the CBD-specific cannabinoid-sensitive visualization reagent; 2) removing the test strip from the liquid sample and allowing it to develop for a defined amount of time; and 3) comparing the intensity of the resulting color change, or absorbance shift, of the test strip to a calibrated quantification reference chart, such that comparison of the color intensity change or absorbance shift of the test sample to calibrated quantification reference chart allows determination of the CBD concentration in the test sample. The calibrated quantification reference chart may be produced, for instance, by contacting a series of calibrated samples having pre-determined CBD concentrations with a series of test strips under the exact same conditions as to be used for the test sample, including using the same CBD-specific cannabinoid-sensitive visualization reagent, the same liquid solvent, and the same color development time as to be used for the test sample. The CBD-specific cannabinoid-sensitive visualization reagent may be a strong base. The CBD-specific cannabinoid-sensitive visualization reagent may be a KOH. The permissive liquid solvent may be an alcohol. The appropriate liquid solvent may be methanol, ethanol, or isopropanol.

In another aspect of the invention, there is provided a method for quantification of CBD in a solid sample, the method involves: 1) contacting a defined amount of solid sample with a defined volume of an extraction solvent for a defined amount of time, wherein CBD is extracted from the solid sample into the extraction solvent resulting in a CBD-containing liquid extraction solution, and wherein the extraction solvent has a composition suitable to allow the reaction of the extracted CBD with a CBD-specific cannabinoid-sensitive visualization reagent; 2) contacting the resulting liquid extraction solution with a test strip comprising a porous matrix uniformly impregnated with a CBD-specific cannabinoid-sensitive visualization reagent; 3) removing the test strip from the liquid extraction solution and allowing it to develop for a defined amount of time; and 4) comparing the intensity of the resulting color change, or absorbance shift, of the test strip to a calibrated quantification reference chart, such that comparison of the color intensity change or absorbance shift of the test sample to a calibrated quantification reference chart allows determination of the CBD concentration in the test sample. The calibrated quantification reference chart may be created by performing the identical method as used on the unknown solid sample on a series of solid samples of known CBD concentration, and recording the resultant color change, or absorbance shift, caused by the known CBD concentrations. The CBD-sensitive visualization reagent may be a strong base. The CBD-specific cannabinoid-sensitive visualization reagent may be a KOH. The extraction solvent may be an alcohol. The extraction solvent may be methanol, ethanol, or isopropanol.

The inventors further disclose that test papers or strips impregnated with a strong base such as KOH rapidly lose effectiveness towards CBD when exposed for only a short time to ambient air. This means that such strips may only be effective when freshly prepared, which is a significant limitation for the applicability in field tests or in kits. The inventors have successfully extended the shelf life of such test strips by vacuum sealing to remove any air and/or moisture from contacting the strips, allowing their use days, weeks, or months after preparation. In certain embodiments, there is provided a CBD-sensitive test paper and/or strip comprising a porous matrix uniformly impregnated with a CBD-sensitive visualization reagent, wherein the test paper and/or strip is provided in a sealed container or package. The sealed container or package may include a dessicant.

THC Test Papers and Strips

The inventors also provide examples of compositions and methods for quantifying cannabinoids THC, CBD and/or CBN in a test sample, using test strips comprising a porous matrix impregnated with cannabinoid-sensitive visualization reagents. In certain embodiments of the invention, the test strip comprises multiple test papers wherein each test paper is impregnated with a different cannabinoid-sensitive visualization reagent.

In other aspects of the invention, the one or more cannabinoid-sensitive visualization reagents is a diazonium salt. In other embodiments, one of the cannabinoid-sensitive visualization reagents is a Ghamrawy reagent or a modified Ghamrawy reagent. The inventors have developed a method for manufacturing test papers with a modified Ghamrawy reagent. Such reagents have been described as requiring hydrochloric acid or sulfuric acid to be effective. As these acids are generally only present in liquid form, these reagents have previously only been suitable for liquid based reactions. The inventors have identified strong acids that may also exist as a solid, for instance p-toluenesulfonic acid. Thus, in certain embodiments, the modified Ghamrawy reagent comprises p-DMAB and p-toluenesulfonic acid. In certain embodiments, the test paper is manufactured by dissolving the modified Ghamrawy reagents in a solvent such as methanol—either together or separately—and then contacting the test paper with the reagent and allowing to dry. The test strip may be heated during the drying process, which the inventors have shown to improve the effectiveness of the test papers. In other embodiments, the test strips may comprise a Duquenois reagent.

In other aspects of the invention, there is thus provided an apparatus which includes a test strip, wherein the test strip comprises a porous matrix uniformly impregnated with one or more cannabinoid-sensitive visualization reagents. In certain embodiments, the one or more cannabinoid-sensitive visualization reagents are present on the test strip in sufficient amount to cause a colorimetric chemical reaction when contacted with cannabinoids and an appropriate solvent. In some embodiments, the cannabinoid-sensitive visualization reagents are present in sufficient amount to allow quantification of THC and/or CBD and/or CBN in a cannabinoid containing sample. In certain embodiments, the one or more visualization reagents are present in different discrete regions of the test strip, for instance on separate test papers that are affixed to the test strip. In certain embodiments, the cannabinoid-sensitive visualization reagents are diazonium salts such as Fast Blue B, Fast Blue BB, Fast Garnet, and/or Fast Corinth V. In certain embodiments, the cannabinoid-sensitive visualization reagent may also be a Duquenois reagent. In certain embodiments, the cannabinoid-sensitive visualization reagent may be a Ghamrawy reagent or a modified Ghamrawy reagent. In certain embodiments, the test strip further comprises an inert support.

In another aspect of the invention, there is provided a method for quantification of the concentration of one or more cannabinoid compounds in a liquid sample, the method involves: 1) contacting the liquid sample with a test strip comprising a porous matrix uniformly impregnated with one or more cannabinoid-sensitive visualization reagents; 2) removing the test strip from the liquid sample and allowing it to develop for a defined amount of time; and 3) comparing the intensity of the resulting color change, or absorbance shift, of the one or more cannabinoid-sensitive visualization reagents to a calibrated quantification reference chart, such that comparison of the color intensity change or absorbance shift of the test sample to the calibrated quantification reference chart allows determination of the cannabinoid concentration in the test sample. The calibrated quantification reference chart may be produced, for instance, by contacting a series of calibrated samples having pre-determined cannabinoid concentrations with a series of test strips under the exact same conditions as to be used for the test sample, including using the same one or more cannabinoid-visualization reagents and the same color development time as to be used for the test sample. In certain embodiments, the test strip comprises one or more test papers, each individually impregnated with different cannabinoid-sensitive visualization reagents. The cannabinoid-sensitive visualization reagent may be a diazonium salt. The cannabinoid-sensitive visualization reagent may be chosen from the following: Fast Blue B, Fast Blue BB, Fast Garnet and Fast Corinth V. The cannabinoid-sensitive visualization reagent may be a Duquenois reagent. The cannabinoid compound to be quantified may be THC. In certain embodiments, the cannabinoid-sensitive visualization reagent may be a Ghamrawy reagent or a modified Ghamrawy reagent.

In another aspect of the invention, there is provided a method for quantification of one or more cannabinoid compounds in a solid sample, the method involves: 1) contacting a defined amount of solid sample with a defined volume of an extraction solvent for a defined amount of time, wherein cannabinoids are extracted from the solid sample into the extraction solvent resulting in a cannabinoid-containing liquid extraction solution; 2) contacting the resulting liquid extraction solution with a test strip comprising a porous matrix uniformly impregnated with one or more cannabinoid-sensitive visualization reagents; 3) removing the test strip from the liquid extraction solution and allowing it to develop for a defined amount of time; and 4) comparing the intensity of the resulting color change, or absorbance shift, of the cannabinoid-sensitive visualization reagent to a calibrated quantification reference chart, such that comparison of the color intensity change or absorbance shift of the test sample to a calibrated quantification reference chart allows determination of the cannabinoid concentration in the test sample. The calibrated quantification reference chart may be created by performing the identical method as used on the unknown solid sample on a series of solid samples of known cannabinoid concentration, and recording the resultant color change, or absorbance shift, caused by the known cannabinoid concentrations. In certain embodiments, the test strip comprises one or more test papers, each individually impregnated with different cannabinoid-sensitive visualization reagents. The cannabinoid-sensitive visualization reagent may be a diazonium salt. The cannabinoid-sensitive visualization reagent may be chosen from the following: Fast Blue B, Fast Blue BB, Fast Garnet and Fast Corinth V. The cannabinoid compound to be quantified may be THC. The cannabinoid-sensitive visualization reagent may be a Duquenois reagent. The cannabinoid compound to be quantified may be THC. In certain embodiments, the cannabinoid-sensitive visualization reagent may be a Ghamrawy reagent or a modified Ghamrawy reagent Kits In another aspect of the invention, there is provided a kit for quantification of the concentration of one or more cannabinoid compounds in a sample, the kit comprising: 1) optionally, a solvent for extraction of cannabinoid compounds from a solid sample; 2) one or more cannabinoid-sensitive visualization reagent; and 3) a calibrated quantification reference chart. In a further embodiment, the calibrated quantification reference chart may be replaced by an instruction or set of instructions guiding or directing to a calibrated quantification reference chart, for instance via web link, URL, email address, or other means. In certain embodiments, the extraction solvent has a composition that is permissive for a visualization reaction with the cannabinoid-sensitive visualization reagents. In certain embodiments, the kit is useful for the quantification of THC in a test sample, and the one or more cannabinoid-sensitive visualization reagents is chosen from: a diazonium salt, for instance Fast Blue B, Fast Blue BB, Fast Corinth V, and Fast Garnet GC; a Duquenois reagent; a Ghamrawy reagent; and/or a modified Ghamrawy reagent. In certain embodiments of the invention the kit is useful for the quantification of CBD in a test sample, and the cannabinoid-sensitive visualization reagent is a strong base, for instance potassium hydroxide or sodium hydroxide. In certain embodiments, the cannabinoid-sensitive visualization reagent is provided in a pre-measured amount suitable for single test reactions. In certain embodiments, the pre-measured cannabinoid-sensitive visualization reagent is provided in dry form. The pre-measured cannabinoid-sensitive visualization reagent may be provided in a ready to use reaction vessel, for instance a test tube, plastic tube, eppendorf tube, and the like, or in a separate pouch or container. In certain embodiments, the dry reagent may further include a solid diluent. In certain embodiments, the extraction solvent may have a composition that is: 1) suitable for dissolving the dry pre-measured cannabinoid-sensitive visualization reagent; and 2) permissive for a visualization reaction between the cannabinoid and the cannabinoid-sensitive visualization reagent.

In another aspect of the invention, there is provided a kit for extended range quantification of the concentration of one or more cannabinoid compounds in a sample, the kit includes: 1) optionally, a solvent for extraction of cannabinoid compounds from the sample; 2) two or more cannabinoid-sensitive visualization reagents; and 3) a calibrated quantification reference chart, wherein the calibrated quantification reference chart comprises calibrated quantification reference for each of the two or more cannabinoid-sensitive visualization reagents. In a further embodiment, the calibrated quantification reference chart may be replaced by an instruction or set of instructions guiding or directing to a calibrated quantification reference chart, for instance via web link, URL, email address, or other means. In certain embodiments, the extraction solvent has a composition that is permissive for a visualization reaction with the two or more cannabinoid-sensitive visualization reagents. In certain embodiments, the kit is useful for the quantification of THC in a test sample, and the cannabinoid-sensitive visualization reagents are chosen from: a diazonium salt, for instance Fast Blue B, Fast Blue BB, Fast Corinth V, and Fast Garnet GC; a Duquenois reagent; a Ghamrawy reagent; and/or a modified Ghamrawy reagent. In certain embodiments, the cannabinoid-sensitive visualization reagent is provided in a pre-measured amount suitable for a single test reaction. In certain embodiments, the pre-measured cannabinoid-sensitive visualization reagent is provided in dry form. The dry reagent may further include a solid diluent. The pre-measured cannabinoid-sensitive visualization reagent may be provided in a ready to use reaction vessel, for instance a test tube, plastic tube, eppendorf tube, and the like, or may be provided in a separate pouch or container. In certain embodiments, the extraction solvent may have a composition that is 1) suitable for dissolving the dry pre-measured cannabinoid-sensitive visualization reagent; and 2) permissive for a visualization reaction between the cannabinoid and the cannabinoid-sensitive visualization reagent.

The following examples are provided for illustrative purposes, and are not intended to be limiting.

EXAMPLES

Example 1—Quantification of THC Content of an Unknown Solid *Cannabis* Sample Using the Compositions and Methods of the Invention—Visualization in Solution Preparation of Cannabinoid-Sensitive Visualization Reagents Fast Blue BB diazonium salt was dissolved in methanol to a final concentration of 0.1%.

Production of Calibrated Quantification Reference Chart

Solid *cannabis* samples with known THC concentration were used to create the calibrated quantification reference chart. These *cannabis* samples were known to have negligible concentrations of other cannabinoids that might also react with the cannabinoid-sensitive visualization reagent, such as CBD or CBN. For each sample, the following protocol was followed to extract the THC into a liquid THC containing solution. The solid sample was macerated into small pieces, and a portion was wrapped in aluminium foil. This was heated at 325° F. for exactly 5 minutes. The resulting solid sample was removed from the foil, crumbled, and a 0.1 g portion was placed into a plastic tube. Exactly 5.0 mL of methanol or isopropanol was placed into the plastic tube. The tube with the 0.1 g solid sample and 5.0 mL of methanol or isopropanol was shaken vigorously for 30 seconds. A 1.0 mL aliquot of the resulting THC containing extraction solution was transferred to an eppendorf tube. One drop (~20 uL) of cannabinoid-sensitive visualization reagent from step A was added, and the reaction was allowed to develop for exactly 10 minutes. This procedure was completed in parallel with a number of solid *cannabis* samples having different known THC concentrations. After the colour development step, all the resulting color reactions were used to create the calibrated quantification reference chart shown in FIG. 1. The colors from each tube are then easily transferred to a suitable medium, for instance onto a reference card and the like, for ease of comparison at any future point. More specifically, as shown in FIG. 1, the calibrated quantification reference chart for THC samples is disclosed having an ideal range of 5-20%. The quantification reference chart was generated using Fast Blue BB. The chart shows a light yellow colour at the left side, changing to a darker yellow/orange on the right side.

A. Determination of THC Concentration in Unknown Solid *Cannabis* Sample

A solid *cannabis* sample with unknown THC concentration (and known to have low concentration of other cannabinoids that might react with the cannabinoid-sensitive visualization reagent, such as CBD or cannabinol) was prepared using the exact same methodology as the samples in Step B. The resulting THC-containing extraction liquid was contacted with cannabinoid-sensitive visualization reagent from Step A and color development for 10 minutes, exactly as in Step B. The resulting color change was then compared to the calibrated quantification reference chart from Step B to determine the THC concentration in the unknown sample.

Example 2—Quantification of THC Content of an Unknown Solid *Cannabis* Sample Using an Extended Range Calibrated Quantification Reference Chart—Visualization in Solution A. Preparation of Two Cannabinoid-Sensitive Visualization Reagents Fast Blue BB salt was dissolved in methanol to a final concentration of 0.1%. Fast Corinth V was dissolved in methanol to a final concentration of 0.1%

B. Production of Calibrated Quantification Reference Chart

Figure 2:
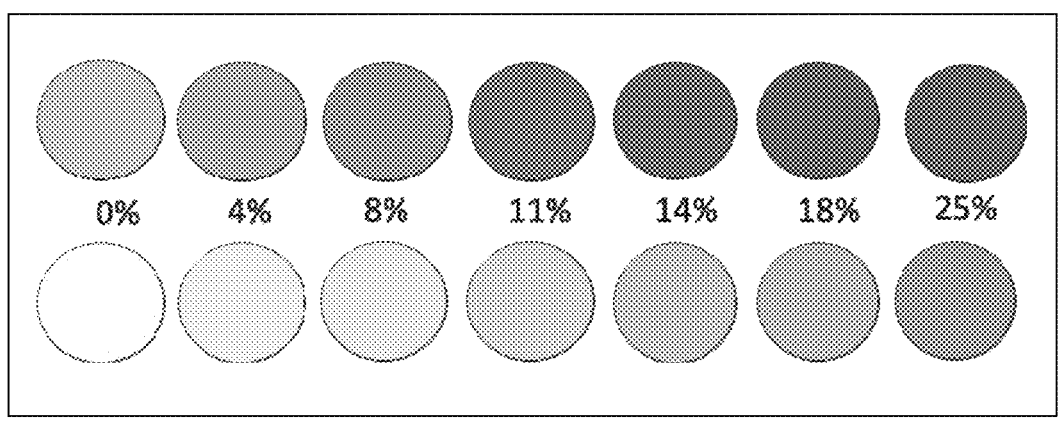
FIG. 2 depicts an extended range calibrated quantification reference chart. The chart includes overlapping ranges for 2 different cannabinoid-sensitive visualization reagents, to allow for quantification from 0% to over 25% THC in a solid sample.

Solid *cannabis* samples with known THC concentration were used to create the calibrated quantification reference chart. These *cannabis* samples were known to have negligible concentrations of other cannabinoids that might also react with the cannabinoid-sensitive visualization reagent, such as CBD or cannabinol. For each sample, the following protocol was followed to extract the THC into a liquid THC containing solution. The solid sample was macerated into small pieces, and a portion was wrapped in aluminium foil. This was heated at 325 degrees Celsius for exactly 5 minutes. The resulting solid sample was removed from the foil, crumbed, and a 0.1 g portion was placed into a plastic container. Exactly 5.0 mL of methanol or isopropanol was placed into the plastic container. The container with the 0.1 g solid sample and 5.0 mL of methanol or isopropanol was shaken vigorously for 10 seconds. A 1.0 mL aliquot of the resulting THC containing extraction solution was transferred to a first eppendorf tube, and a 1.0 mL aliquot of the resulting THC containing extraction solution was transferred to a second eppendorf tube. One drop (~20 uL) of Fast Blue BB cannabinoid-sensitive visualization reagent from step A was added to the first eppendorf tube, and one drop (~20 uL) of Fast Corinth V cannabinoid-sensitive visualization reagent from step A was added to the second eppendorf tube, and the reaction in each tube was allowed to develop for exactly 10 minutes. This procedure was completed in parallel with a number of solid *cannabis* samples having different known THC concentrations. After the colour development step, all the resulting color changes for Fast Blue BB, and the resulting color changes for Fast Corinth V were used to create the extended range calibrated quantification reference chart (FIG. 2). More specifically, as shown in FIG. 2, an extended range calibrated quantification reference chart is detailed therein. The chart includes overlapping ranges for 2 different cannabinoid-sensitive visualization reagents, to allow for quantification from 0% to over 25% THC in a solid sample. The top row of colors is generated using Fast Corinth V. The bottom row of colors is generated using Fast Blue BB. The top row, moving from left to right, shows the color change starting as light orange at the bottom of the range and getting progressively more red at the top of the range. The ideal quantification range for the top row is 0-14%. The bottom row, moving from left to right, shows the color change starting at light yellow at the bottom of the range, and moving to darker orange at the top of the range. The ideal quantification range is 11-25%. The overlapping ideal ranges provides good quantification between 0-25% THC.

C. Determination of THC Concentration in Unknown Solid *Cannabis* Sample

A solid *cannabis* sample with unknown THC concentration (and known to have low concentration of other cannabinoids that might react with the cannabinoid-sensitive visualization reagent, such as CBD or cannabinol) was prepared using the exact same methodology as the samples in Step B. The resulting THC-containing extraction liquid was contacted with cannabinoid-sensitive visualization reagent from Step A and colour development for 10 minutes, exactly as in Step B. The resulting colour change was then compared to the extended range calibrated quantification reference chart from Step B to determine the THC concentration in the unknown sample.

Example 3—Quantification of CBD Content of an Unknown Solid *Cannabis* Sample Using the Compositions and Methods of the Invention—Visualization in Solution A. Preparation of Cannabinoid-Sensitive Visualization Reagent Potassium hydroxide was dissolved in water to a final concentration of 20%.

B. Production of Calibrated Quantification Reference Chart

Figure 3:
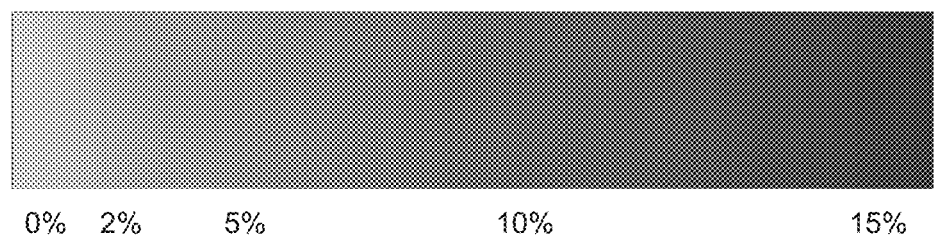
FIG. 3 depicts a calibrated quantification reference chart for CBD samples having ideal range 0-15%. Moving from left to right, the figure shows the color changing from very light purple at the lower end of the scale to a much darker purple at the higher end of the scale.

Solid *cannabis* samples with known CBD concentration were used to create the calibrated quantification reference chart. For each sample, the following protocol was followed to extract the CBD into a liquid CBD containing solution. The solid sample was macerated into small pieces, and a portion was wrapped in aluminium foil. This was heated at 325 degrees Celsius for exactly 5 minutes. The resulting solid sample was removed from the foil, crumbed, and a 0.1 g portion was placed into a plastic container. Exactly 3.0 mL of methanol or isopropanol was placed into the plastic container. The container with the 0.1 g solid sample and 3.0 mL of methanol or isopropanol was shaken vigorously for 10 seconds. A 1.0 mL aliquot of the resulting THC containing extraction solution was transferred to an eppendorf tube. Two drops (~40 uL) of cannabinoid-sensitive visualization reagent potassium hydroxide from step A was added, and the reaction was allowed to develop for exactly 10 minutes. This procedure was completed in parallel with a number of solid *cannabis* samples having different known CBD concentrations. After the colour development step, all the resulting reactions were lined up in order of increasing THC concentration and the colors used to create the calibrated quantification reference chart (FIG. 3). The colors from each tube are then easily transferred to a suitable medium, for instance onto a reference card and the like, for ease of comparison at any future point. More specifically, as shown in FIG. 3, a calibrated quantification reference chart for CBD samples is depicted demonstrating an ideal range of 0-15%. Moving from left to right, the figure shows the color changing from very light purple at the lower end of the scale to a much darker purple at the higher end of the scale.

C. Determination of THC Concentration in Unknown Solid *Cannabis* Sample

A solid *cannabis* sample with unknown CBD concentration was prepared using the exact same methodology as the samples in Step B. The resulting CBD-containing extraction liquid was contacted with cannabinoid-sensitive visualization reagent from Step A and colour development for 10 minutes, exactly as in Step B. The resulting colour change was then compared to the extended range calibrated quantification reference chart from Step B to determine the CBD concentration in the unknown sample.

Example 4—Quantification of THC Content of an Unknown Solid *Cannabis* Sample Using the Compositions and Methods of the Invention A. Preparation of Test Strips Impregnated with Fast Blue BB Fast Blue BB salt was dissolved in methanol to a final concentration of 1%. Strips of Whatman paper (CF2) were submersed in the 1% Fast Blue BB methanol solution, removed, and allowed to dry.

B. Production of Calibrated Quantification Reference Chart

Figure 4:
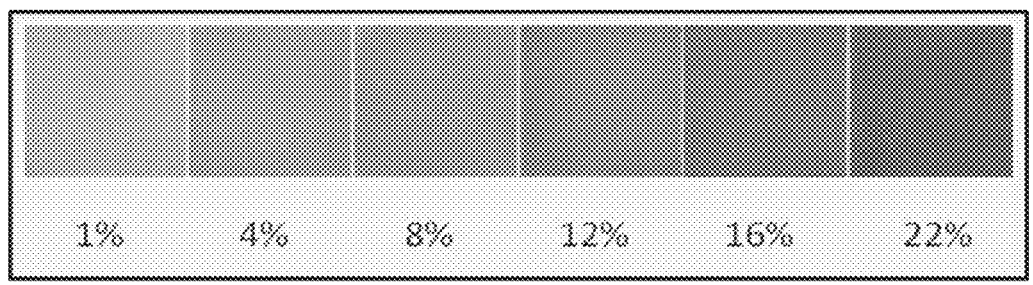
FIG. 4 depicts a calibrated reference chart for Fast BB impregnated test strips. The chart shows that, moving from left to right, the color change of the strip goes from a very light orange/red at the low end of the scale to a much darker red at the higher end of the scale.

Solid *cannabis* samples with known THC concentration were used to create the calibrated quantification reference chart. For each sample, the following protocol was followed to extract the THC into a liquid THC containing solution. The solid sample was macerated into small pieces, and a portion was wrapped in aluminium foil. This was heated at 325 degrees Celsius for exactly 5 minutes. The resulting solid sample was removed from the foil, crumbed, and a 0.1 g portion was placed into a plastic container. Exactly 15 mL of methanol or isopropanol was placed into the plastic container. The container with the 0.1 g solid sample and 15 mL of methanol or isopropanol was shaken vigorously for 10 seconds. A 1.5 mL aliquot of the resulting THC containing extraction solution was transferred to an eppendorf tube. An unused Fast Blue impregnated test strip from Part A was dipped briefly into the THC containing extraction solution, and excess liquid was shaken off the test strip. The test strip was allowed to air dry and the colour was allowed to develop for exactly 10 minutes from the point where the strip first touched the THC containing extraction solution. This procedure was completed in parallel with a number of solid *cannabis* samples having different known THC concentrations. After the colour development step, all the resulting test strips were lined up in order of increasing THC concentration, and a picture taken to create the calibrated quantification reference chart—see FIG. 4. More specifically, as shown in FIG. 4, a calibrated reference chart for Fast BB impregnated test strips is depicted. The chart shows that, moving from left to right, the color change of the strip goes from a very light orange/red at the low end of the scale to a much darker red at the higher end of the scale.

C. Determination of THC Concentration in Unknown Solid *Cannabis* Sample

A solid *cannabis* sample with unknown THC concentration was prepared using the exact same methodology as the samples in Step B. The resulting THC-containing extraction liquid was tested by dipping a Fast Blue BB impregnated test strip from Step A briefly into the THC containing extraction liquid, removing excess liquid, and allowing air drying and colour development for 10 minutes, exactly as in Step B. The resulting colour change was then compared to the calibrated quantification reference chart from Step B to determine the THC concentration in the unknown sample.

Figure 5:
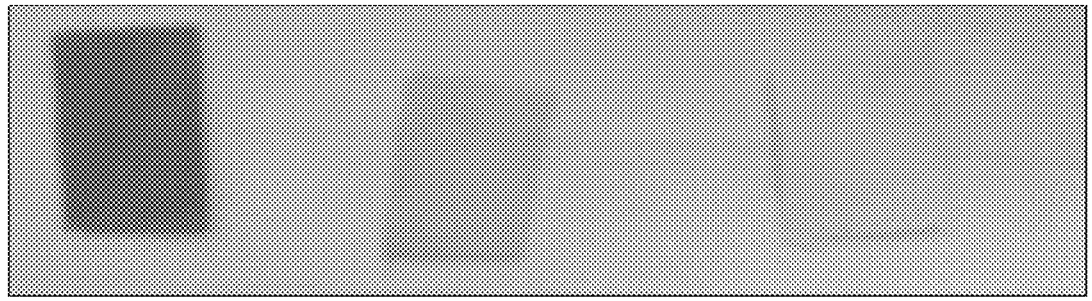
FIG. 5 depicts representative test papers prepared using 30% KOH (left), 10% KOH (middle), and 1% KOH (right).

Example 5—Quantification of CBD Content of an Unknown Solid *Cannabis* Sample Using the Compositions and Methods of the Invention A. Preparation of Test Strips Impregnated with KOH KOH was dissolved in methanol to a final concentration between 1-30% methanol (1%, 10%, 30%). Strips of Whatman paper (CF1) were submersed in the KOH solution, removed, and allowed to dry. Dried test strips were dipped in a methanol extract of a CBD containing *Cannabis* sample. The *Cannabis* sample contained 15% CBD and the extract was prepared by i) macerating the sample and heating at 325 degrees Fahrenheit for 5 minutes to convert CBD-A to CBD; ii) adding 0.1 g of the heated sample to 1.0 mL of methanol; and iii) shaking vigorously for 20 seconds. After the test strips were dipped in the CBD liquid extract, they were allowed to develop for 5 minutes. FIG. 5 shows that impregnation of the test strips using 1% or 10% KOH in methanol did not result in a significant color change in the subsequent reaction with the CBD liquid extract, however using 30% did allow for a significant colorimetric reaction to occur. More specifically, as shown in FIG. 5, representative test papers are depicted having been prepared using 30% KOH (left), 10% KOH (middle), and 1% KOH (right).

B. Production of Calibrated Quantification Reference Chart

Figure 6:
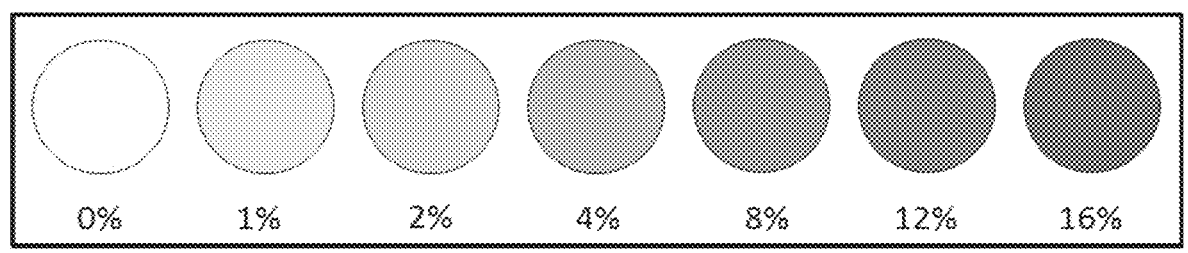
FIG. 6 depicts a CBD Calibrated Reference Chart. Moving from left to right on the chart, the color change shown on the chart goes from a very light violet/purple for the lower CBD % to a much darker purple for higher CBD %.

Solid *cannabis* samples with known CBD concentration were used to create the calibrated quantification reference chart. For each sample, the following protocol was followed to extract the CBD into a liquid CBD containing solution. The solid sample was macerated into small pieces, and a portion was wrapped in aluminium foil. This was heated at 325 degrees Fahrenheit for exactly 5 minutes. The resulting solid sample was removed from the foil, crumbled, and a 0.1 g portion was placed into a plastic container. Exactly 1.0 mL of methanol or isopropanol was placed into the plastic container. The container with the 0.1 g solid sample and 1.0 mL of methanol or isopropanol was shaken vigorously for 20 seconds. An aliquot of the resulting CBD containing extraction solution was transferred to an eppendorf tube. A KOH impregnated test strip was prepared as in Part A, except that the impregnation of the test strips was performed with KOH dissolved in methanol at a concentration of 20% w/v. An unused KOH impregnated test strip was dipped briefly into the CBD containing extraction solution, and excess liquid was shaken off the test strip. The test strip was allowed to air dry and the color was allowed to develop for exactly 5 minutes from the point where the strip first touched the CBD containing extraction solution. This procedure was completed in parallel with a number of solid *cannabis* samples having different known CBD concentrations. After the color development step, all the resulting test strips were lined up in order of increasing CBD concentration, and a picture taken to create the calibrated quantification reference chart—see FIG. 6. It can be seen that the color intensity increases in direct correlation with the increasing CBD concentration in the sample. More specifically, as shown in FIG. 6, a CBD Calibrated Reference Chart is depicted. Moving from left to right on the chart therein, the color change shown on the chart goes from a very light violet/purple for the lower CBD % to a much darker purple for higher CBD %.

C. Determination of CBD Concentration in Unknown Solid *Cannabis* Sample

A solid *cannabis* sample with unknown CBD concentration was prepared using the exact same methodology as the samples in Step B. The resulting CBD-containing extraction liquid was tested by dipping a KOH impregnated test strip from Step A briefly into the CBD containing extraction liquid, removing excess liquid, and allowing air drying and color development for 5 minutes, exactly as in Step B. The resulting color change was then compared to the calibrated quantification reference chart from Step B to determine the CBD concentration in the unknown sample.

Example 6—Quantification of THC Content of an Unknown Solid *Cannabis* Sample Using the Compositions and Methods of the Invention A. Preparation of Test Papers Impregnated with Modified Ghamrawy Reagent A 10% solution of p-dimethylaminobenzaldehyde (p-DMAB) in methanol was prepared in a tube. In a separate tube, a 5M solution of p-toluenesulfonic acid in methanol was prepared. Squares of CF4 paper (GE Healthcare) were immersed in the p-DMAB solution and allowed to dry, and then quickly dipped in the p-toluenesulfonic acid solution. The strips were then placed in an oven at 200 degrees Fahrenheit for 2 minutes until the strips were completely dry.

B. Preparation of Calibrated Reference Chart

Figure 7:
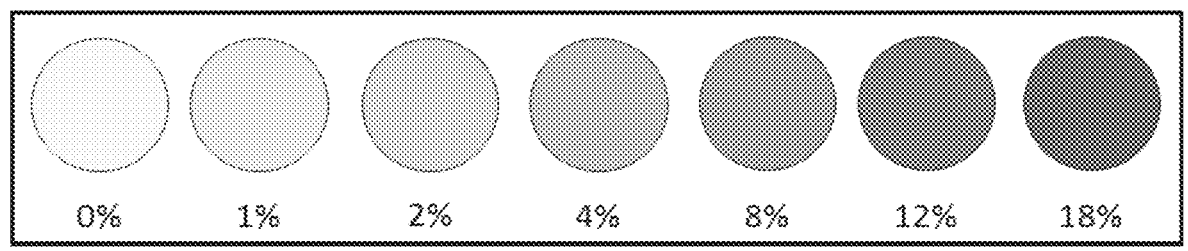
FIG. 7 depicts a THC Calibrated Reference Chart using modified Ghamrawy reagent impregnated test papers. Moving from left to right on the chart, the color change shown on the chart goes from a very light violet/purple for the lower THC % to a much darker purple for higher THC %.

Solid *cannabis* samples with known THC concentration were used to create the calibrated quantification reference chart. For each sample, the following protocol was followed to extract the THC into a liquid THC containing solution. The solid sample was macerated into small pieces, and a portion was wrapped in aluminium foil. This was heated at 325 degrees Celsius for exactly 5 minutes. The resulting solid sample was removed from the foil, crumbed, and a 0.1 g portion was placed into a plastic container. Exactly 15 mL of methanol or isopropanol was placed into the plastic container. The container with the 0.1 g solid sample and 15 mL of methanol or isopropanol was shaken vigorously for 10 seconds. A 1.5 mL aliquot of the resulting THC containing extraction solution was transferred to an eppendorf tube. An unused modified Ghamrawy reagent impregnated test strip from Part A was dipped briefly into the THC containing extraction solution, and excess liquid was shaken off the test strip. The test strip was allowed to air dry and the colour was allowed to develop for exactly 10 minutes from the point where the strip first touched the THC containing extraction solution. This procedure was completed in parallel with a number of solid *cannabis* samples having different known THC concentrations. After the colour development step, all the resulting test strips were lined up in order of increasing THC concentration, and a picture taken to create the calibrated quantification reference chart—see FIG. 7. More specifically, as shown in FIG. 7, a THC Calibrated Reference Chart using modified Ghamrawy reagent impregnated test papers is depicted. Moving from left to right on the chart therein, the color change shown on the chart goes from a very light violet/purple for the lower THC % to a much darker purple for higher THC %.

C. Quantification of THC Concentration in a Test Sample of Unknown Concentration A solid *cannabis* sample with unknown THC concentration (and known to have low concentration of other cannabinoids that might react with the cannabinoid-sensitive visualization reagent, such as CBD) was prepared using the exact same methodology as the samples in Step B. The resulting THC-containing extraction liquid was contacted with cannabinoid-sensitive visualization reagent from Step A and colour development for 10 minutes, exactly as in Step B. The resulting colour change was then compared to the calibrated quantification reference chart from Step B to determine the THC concentration in the unknown sample.

While specific embodiments of the invention have been described and illustrated, such embodiments should be considered illustrative of the invention only and not as limiting the invention as construed in accordance with the accompanying claims. Other features and advantages of the invention will be apparent from the following description of the drawings and the invention, and from the claims.

What is claimed is:

1. A method for quantifying a concentration of one or more cannabinoid compounds in a solid test sample, the method comprising:
   contacting the solid test sample with a lower alcohol extraction solvent, wherein one or more cannabinoid compounds are extracted from the solid test sample into the extraction solvent resulting in a cannabinoid-containing liquid extraction solution;
   contacting the cannabinoid-containing liquid extraction solution with one or more cannabinoid-sensitive visualization reagents, wherein the one or more cannabinoid-sensitive visualization reagents comprise p-dimethylaminobenzaldehyde (p-DMAB) and p-toluenesulfonic acid, impregnated and dried on a test strip;
   comparing a resulting color change of the one or more cannabinoid-sensitive visualization reagents to a calibrated quantification reference chart, wherein the calibrated reference chart is calibrated by color to correspond to a range of concentrations of the one or more cannabinoid compounds; and
   determining the concentration of the one or more cannabinoid compounds in the solid test sample by the resulting color change.

2. The method of claim 1, wherein the range of concentrations of the one or more cannabinoid compounds is between about 0% to about 25% of the one or more cannabinoid compounds.

3. The method of claim 1, wherein the one or more cannabinoid compounds comprises cannabidiol.

4. The method of claim 3, wherein the range of concentration of the cannabidiol is between about 0% to about 25%.

5. The method of claim 4, wherein the lower alcohol extraction solvent is methanol.

6. The method of claim 1, wherein the lower alcohol extraction solvent consists essentially of methanol, ethanol, propanol, or isopropanol.

7. The method of claim 1, wherein the lower alcohol extraction solvent is methanol or isopropanol.

8. The method of claim 1, wherein the lower alcohol extraction solvent is methanol.

9. The method of claim 1, wherein the one or more cannabinoid-sensitive visualization reagents further comprise two or more cannabinoid-sensitive visualization reagents.

10. The method of claim 9, wherein the extraction solvent consists essentially of methanol or isopropanol.

11. The method of claim 9, wherein the extraction solvent is methanol.

12. The method of claim 9, wherein the range of concentrations of the one or more cannabinoid compounds is between about 0% to about 25% of the one or more cannabinoid compounds.

13. The method of claim 12, wherein the range of concentrations of the one or more cannabinoid compounds is between 0% to about 15% of the one or more cannabinoid compounds.

14. The method of claim 9, wherein the one or more cannabinoid compounds comprise cannabidiol.

15. The method of claim 14, wherein the range of concentrations of the one or more cannabinoid compounds is between about 0% to about 25% of the one or more cannabinoid compounds.

16. The method of claim 15, wherein the range of concentrations of the one or more cannabinoid compounds is between 0% to about 15% of the one or more cannabinoid compounds.

17. The method of claim 9, wherein the one or more cannabinoid compounds comprise tetrahydrocannabinol.

* * * * *